July 13, 1954 D. J. GREER Plant Pat. 1,288
POTHOS PLANT
Filed Feb. 2, 1953
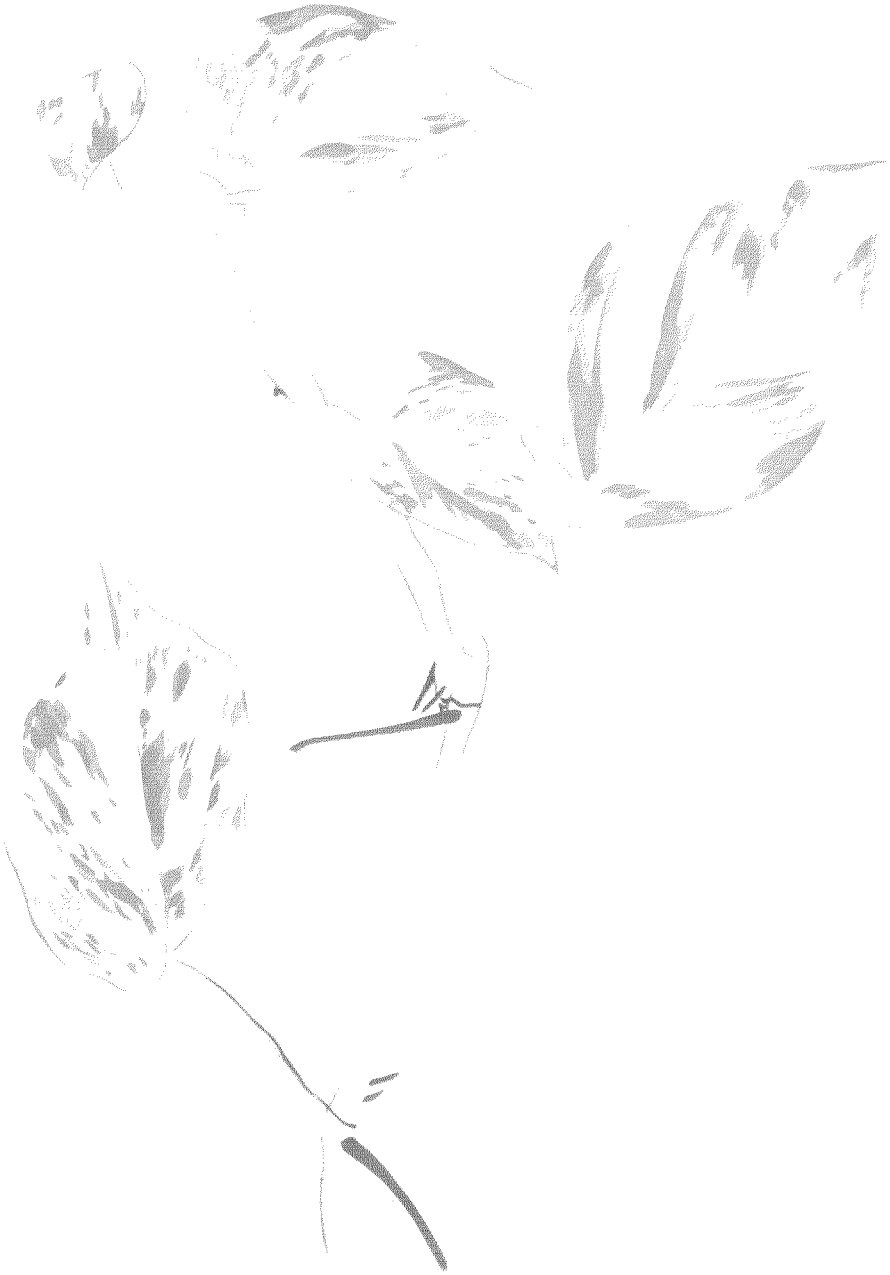
INVENTOR
Daniel J. Greer
By Orville M. Kile
plant patent Agt.

Patented July 13, 1954 Plant Pat. 1,288

UNITED STATES PATENT OFFICE 1,288

POTHOS PLANT

Daniel J. Greer, Hialeah, Fla.

Application February 2, 1953, Serial No. 334,772

1 Claim. (Cl. 47—59)

This new and distinct variety of plant, of which I am the discoverer, belongs to the class of tropical vines or herbaceous shrubs known as Pothos. My new variety is a sport of the variety Aureus and I discovered it on one of the plants growing in one of my slat houses in Miami, Florida. I took steps to protect and observe this sport and to propagate it by cuttings at my nurseries, and have demonstrated that it successfully reproduces asexually. Not only is it a new and pleasing variety but it has exceptional reproductive qualities.

The accompanying illustrations show, in approximately natural size and as true to coloring as the artist was able to make it, a terminal spray or branch of my new variety, with three typical terminal leaves and a partly developed leaf. Also at the lower left is shown a single comparable leaf of the variety Marble Queen (unpatented) to indicate the contrasting features.

The following is a description of my new variety of Pothos, with detailed emphasis on the essential features. All color reference (other than common dictionary terms) are to Ridgway's Color Standards and Nomenclature.

*Flowers.*—No variety of Pothos observed by me in Florida, and to the best of my knowledge by anyone else here, has ever produced flowers, although they may do so in the tropics.

*The plant.*—It is the usual Pothos type and is an evergreen vine with heavy stems that will grow to great height when trained against a post, tree or wall where the strong greenish-brown cordlike aerial roots can attach themselves. The parent variety (Aureus) readily grows to a height of forty or fifty feet over the years and produces thick, heavy leaves that may be two feet or more in length and almost as wide. This new variety is a rapid grower and gives every indication of equaling its parent in this respect.

However, Pothos is chiefly valuable commercially for its use as a rapidly growing young potted plant. It is the younger terminal growth that shows the most distinctive coloring in this new variety, although the older leaves retain the distinguishing features.

*Leaves.*—The younger leaves of my new variety are cordate, with acute apex and a midrib dividing the leaves unevenly, usually one side being much larger than the other side. Petioles of the terminal several leaves are two to three inches long and flat or channeled on the upper side, this channel being bordered by a thin tissue-like growth, greenish-white in color in the youngest leaves but after a few days shrivelling and falling off and leaving only a brown line edging the channel.

*Color.* — Leaves have sharply contrasting whites, yellows and greens, occurring sometimes as splotches but mostly tending toward areas definitely outlined by veinings, right and left sides of a leaf usually differing greatly in color arrangements. The predominant color effect of an individual leaf is usually either green with yellow and white splotches and markings, or white with green and yellow markings, the markings usually following the general direction of the veins and therefore appearing at a sharp angle to the midrib.

The yellows range from Citron Yellow (Pl. XVI) to Chalcedony Yellow (Pl. XVII) and on to Clear Dull Green-Yellow (Pl. XVII). The small, darkest-green areas are approximately Forest Green (Pl. XVII). Most of the green areas are, however, much lighter, ranging to Javel Green (Pl. V). The "whites" range from almost pure white to creamy white—mostly the latter.

The above description and the illustrations are of leaves in a slat house in Miami at the end of December. The colorings are somewhat brighter in the warmer months.

*Propagation.*—This new variety is a rapid and easy propagator. Cuttings root quickly and grow rapidly. If allowed to grow without cutting back, a newly rooted cutting will grow to approximately eight feet in length in a single year under good southern Florida, slat-protected conditions. It propagates two to three times as rapidly as the variety Marble Queen, which it sometimes resembles, and fully as rapidly as its parent, Aureus.

*Comparisons*

My new variety does not resemble its parent, Aureus, the latter being mostly Forest Green in color and having one or more golden or yellow blotches of considerable size, and no whites.

At first glance my new variety bears some resemblance to the variety Marble Queen. But the two are readily distinguishable by the absence of yellows in Marble Queen; also the tendency in Marble Queen to give a somewhat "marbled" effect—hence the name. Another important difference, valuable to the commercial propagator, is that this new variety will multiply two to three times as rapidly as Marble Queen when grown under the same or similar conditions.

Having thus disclosed my discovery, I claim:

The new and distinct variety of Pothos plant, substantially as herein described and illustrated, characterized particularly by its rapid propagation and quick growth, and its leaves each having sharply contrasting white, yellow and green color-patterns as described rather than a combination of just two of these colors.

No references cited.